US00PP32291P3

(12) United States Plant Patent
Rattanasophon

(10) Patent No.: US PP32,291 P3
(45) Date of Patent: Oct. 6, 2020

(54) ***CURCUMA* PLANT NAMED 'CPH ORANGE'**

(50) Latin Name: ***Curcuma* hybrid**
Varietal Denomination: CPH Orange

(71) Applicant: Chiangmai Plants and Herbs Co., Ltd., Chiangmai (TH)

(72) Inventor: Sasirin Rattanasophon, Chiangmai (TH)

(73) Assignee: Chiangmai Plants and Herbs Co., Ltd., Chiangmai (TH)

( * ) Notice: Subject to any disclaimer, the term of this patent is extended or adjusted under 35 U.S.C. 154(b) by 0 days.

(21) Appl. No.: 16/501,639

(22) Filed: May 15, 2019

(65) Prior Publication Data

US 2019/0357405 P1 Nov. 21, 2019

Related U.S. Application Data

(60) Provisional application No. 62/762,738, filed on May 17, 2018.

(51) Int. Cl.
*A01H 5/02* (2018.01)
*A01H 6/00* (2018.01)

(52) U.S. Cl.
USPC ..... Plt./421

(58) Field of Classification Search
USPC ..... Plt./263.1, 421
See application file for complete search history.

*Primary Examiner* — Susan McCormick Ewoldt
*Assistant Examiner* — Karen M Redden
(74) *Attorney, Agent, or Firm* — The Webb Law Firm

(57) ABSTRACT

A new and distinct *curcuma* plant having orange colored inflorescences.

1 Drawing Sheet

Botanical classification: *Curcuma* hybrid.
Varietal denomination: 'CPH Orange'.

BACKGROUND OF THE INVENTION

The present invention comprises a new and distinct variety of *curcuma* plant known by the varietal name 'CPH Orange' (previously referred to in U.S. Provisional Patent Application No. 62/762,738 as simply "Orange"). The new variety was discovered in 2017 in Chiangmai, Thailand as the result of a planned breeding program with the purposes of providing *curcuma* plants with new coloration and characteristics. The new variety is the result of a cross between an unnamed and unpatented *Curcuma alismatifolia* variety (female parent) and an unnamed and unpatented *Curcuma roscoeana* variety (male parent). The inflorescence color of the new variety is brighter orange than its female parent. Similar to its male parent, 'CPH Orange' exhibits an orange inflorescence color with the presence of a pale cream color in its flowers, but differs from its male parent in having larger and longer inflorescences than its male parent. Tissue culture and bulb asexual reproductions of the new variety first occurred in 2017 in Chiangmai, Thailand. 'CPH Orange' has been trial and field tested and has been found to retain its distinctive characteristics and remain true to type through successive propagations. The present invention has not been evaluated under all possible environmental conditions. The phenotype may vary with variations in environment without a change in the genotype of the plant.

The inflorescence color, large size, and red colored upper surface leaf midrib distinguish 'CPH Orange' from other *curcuma* varieties known to the breeder. Further, when 'CPH Orange' is compared to *Curcuma* hybrid 'CPH Coral' (U.S. Plant patent application Ser. No. 16/501,638), the varieties are similar in plant height. However, the varieties differ in inflorescence color ('CPH Coral' has light pink/coral colored inflorescences) and 'CPH Orange' exhibits a red upper surface leaf midrib that is not exhibited by 'CPH Coral'.

DESCRIPTION OF THE DRAWING

The accompanying photographic drawing taken at approximately 60 days of age illustrates the new variety, with the colors being as nearly true as is possible with color illustrations of this type.

DESCRIPTION OF THE PLANT

The following detailed description sets forth the characteristics of the new variety at approximately 60 days of age. The data which defines these characteristics was collected under natural light in Chiangmai, Thailand. Plants of the new variety were grown in 20.3 cm pots in a plastic greenhouse in Chiangmai, Thailand and watered 1-2 times a day, if needed. Color references are primarily to the 2016 HTML Color Chart and The 2015 R.H.S. Colour Chart of The Royal Horticultural Society of London, 6th Edition, except where general color terms are used.

PLANT

Time to initiate roots: About 20-30 days at about 30-33° C.
Time to produce a rooted young plant: About 45 days at about 30-33° C.
Root description: Fibrous, with a cream colored (C6BDB2) milk tank.
Number of rhizomes produced per plant: From 1-3.
Rhizome diameter: 2.0-3.0 cm.
Growth habit: Annual.
Plant height (soil level to top of inflorescences): 60.0 cm.
Plant diameter: 30.0 cm.
Pubescence: None observed.

Disease resistance/susceptibility: None observed.
Pest resistance/susceptibility: None observed.
Temperature tolerance: 20-40° C. or tropical climate conditions.
Drought tolerance: Unknown.
Seed/fruit: None observed to date.
Leaves:
*Arrangement*.—Alternate.
*Average number per plant*.—From 3-5.
*Length*.—25.0 cm.
*Width*.—7.0 cm.
*Shape of leaf* (*generally*).—Moderately elliptic.
*Shape of apex*.—Attenuate.
*Shape of base*.—Narrow.
*Margin description*.—Entire.
*Texture*.—Upper surface: Smooth. Lower surface: Smooth.
*Aspect*.—Upright.
*Color*.—Young leaves: Upper surface: Green (C5E96E). Lower surface: Green (7BA058). Mature leaves: Upper surface: Green (578441). Lower surface: Green (3B631D).
*Veins*.—Appearance: Pinnate and penninerved. Color: Upper surface: Red (914B41) midrib present. Lower surface: Green (55783C).
*Leaf sheaths*.—Length: 20.0-30.0 cm. Width: 3 cm. Texture: Upper surface: Smooth. Lower surface: Smooth. Color: Upper surface: RHS 142A. Lower surface: RHS 142A. Venation: Pattern: parallel. Color: RHS 59B.

INFLORESCENCE

Inflorescence arrangement: 1 inflorescence per shoot.
Inflorescence number per plant: From 1-3.
Inflorescence length: 20.0 cm.
Inflorescence diameter: 8.0 cm.
Fragrance: None.
Flower bracts:
*Total number per inflorescence*.—Approximately 20.
*Upper bracts*.—Number: Approximately 10. Length: 5.0 cm. Width: 4.0 cm. Shape: Oblong. Apex: Acuminate. Base: Ovate. Margin: Entire. Texture: Upper surface: Smooth. Lower surface: Smooth. Color: Upper surface: RHS 34B. Lower surface: RHS 34B.
*Lower bracts*.—Number: Approximately 10. Length: 3.0 cm. Width: 3.0 cm. Shape: Ovate. Apex: Mucronate. Base: Shallow U-shaped. Margin: Entire. Texture: Upper surface: Smooth. Lower surface: Smooth. Color: Upper surface: Orange (E92830). Lower surface: Orange (F7565E).
Flowers:
*Number per inflorescence*.—Approximately 50.
*Continuity of flowering*.—1 month.
*Lastingness of an individual flower*.—1-2 days.
*Length*.—2.0 cm.
*Diameter*.—2.0 cm.
*Appearance*.—Orchidaceous form.
*Upper petals*.—Upper surface color: Pale cream (FFE7D8). Lower surface color: Pale cream (FFE7D8).
*Lower petals*.—Upper surface color: Cream (FFE4D6) with a yellow (FFFA60) lip. Lower surface color: Cream (FFE4D6).
*Flower buds*.—Length: 4.0 cm. Diameter: 1.5 cm. Shape: Round apex, with the base connected in a cone shape. Texture: Smooth. Color: Generally RHS 4D, with RHS 69D at the tip.
*Sepals*.—Number: 3. Calyx arrangement: In overlapping circles. Length: 1.0 cm. Width: 0.5 cm. Overall shape: Elliptic. Apex: Elliptic. Base: Connected in a cone shape. Texture: Smooth (both surfaces). Color: RHS 4D (both surfaces).
Peduncles:
*Length*.—20.0 cm.
*Diameter*.—1.0 cm.
*Texture*.—Smooth.
*Angle*.—Upright.
*Color*.—Green (827912).

REPRODUCTIVE ORGANS

Stamens:
*Number*.—1.
Filament:
*Length*.—2.0 cm.
*Diameter*.—1.0 mm.
*Color*.—Pale cream (C6AE98).
Anthers:
*Shape*.—2-lobed.
*Length*.—3.0 mm.
*Color*.—Cream (B88967).
Pollen: None observed.
Pistils:
*Number*.—1.
*Length*.—1.0 cm.
Style:
*Length*.—1.0 cm.
*Diameter*.—2.0 mm.
*Color*.—Pale cream (C6AE98).
Stigma:
*Length*.—2.0 mm.
*Diameter*.—2.0 mm.
*Color*.—Pale cream (C6AE98).

I claim:

1. A new and distinct variety of *curcuma* plant, as is herein illustrated and described.

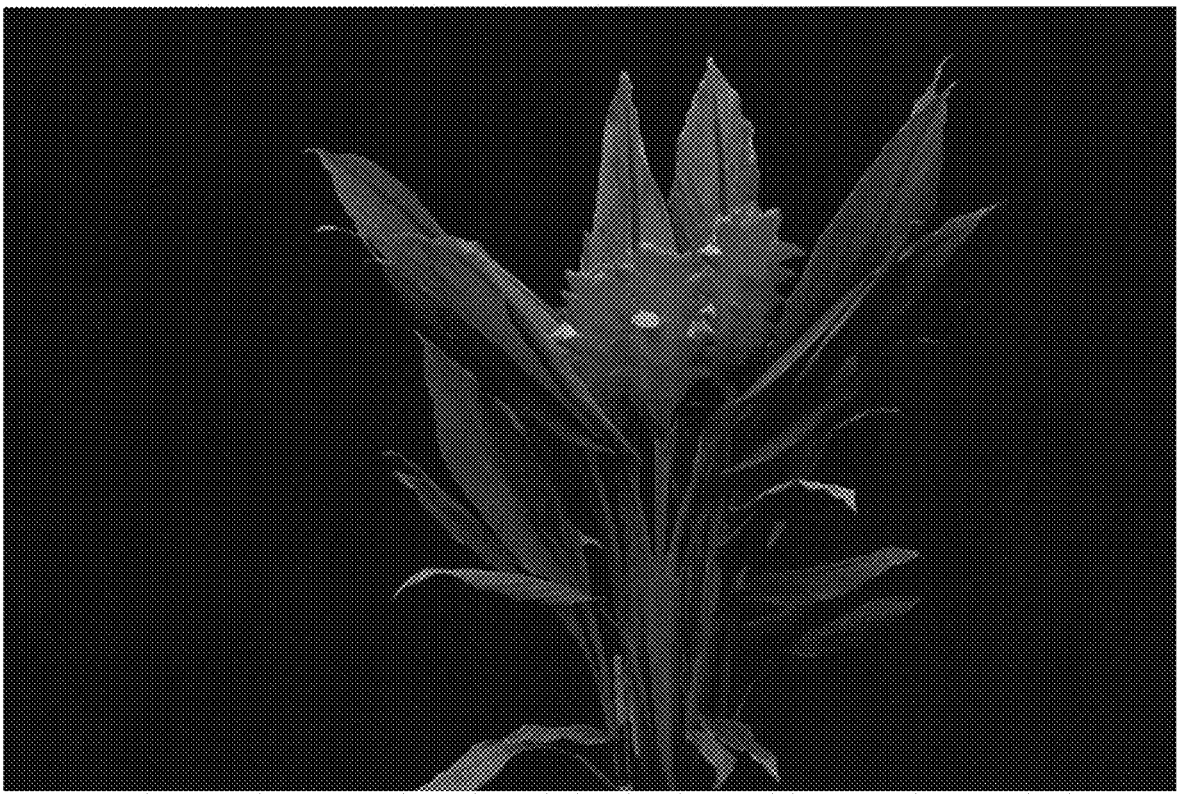

* * * * *